United States Patent [19]

Collier

[11] Patent Number: 4,799,498

[45] Date of Patent: Jan. 24, 1989

[54] APPARATUS FOR DETECTING THE RESONANT FREQUENCY OF A BONE

[75] Inventor: Richard J. Collier, Canterbury, England

[73] Assignees: Kent Scientific; Industrial Project Ltd., both of Kent, England

[21] Appl. No.: 792,470

[22] Filed: Oct. 29, 1985

[30] Foreign Application Priority Data

Nov. 1, 1984 [GB] United Kingdom ................. 8427602

[51] Int. Cl.[4] .................................... A61B 5/10

[52] U.S. Cl. .................................... 128/774; 128/739

[58] Field of Search ............... 128/774, 740, 782, 739, 128/630

[56] References Cited

U.S. PATENT DOCUMENTS

| | | | |
|---|---|---|---|
| Re. 29,008 | 10/1976 | Ott | 128/774 X |
| 2,742,035 | 4/1956 | Hancock et al. | 128/739 |
| 3,477,422 | 11/1969 | Jurist, Jr. et al. | 128/774 X |
| 3,955,404 | 5/1976 | Bickel et al. . | |
| 4,175,546 | 11/1979 | Goldblatt et al. | 128/739 |
| 4,177,798 | 12/1979 | Leveque et al. | 128/774 |
| 4,217,912 | 8/1980 | Hubmann et al. | 128/774 |
| 4,235,243 | 11/1980 | Saha | 128/774 X |
| 4,297,884 | 11/1981 | Leveque et al. | 128/774 X |
| 4,416,269 | 11/1983 | Enomoto et al. | 128/739 X |
| 4,421,119 | 12/1983 | Pratt, Jr. | 128/774 X |

FOREIGN PATENT DOCUMENTS 2156983 10/1985 United Kingdom .

OTHER PUBLICATIONS

Petersen; "Noninvasive Determination of Bone Stiffness"; *Proc. of 7th N.E. Bioengr. Conf.*; 3-1979, pp. 519-522.

Elmessiery et al., "Effects of Measuring System Parameters on the Freq. Dependence of Strain-Related Pot'Ls in Bone"; *Med. & Biol. Eng. & Comput.* 1979, 17, pp. 471-475.

Doherty et al.; "*Evaluation of the use of Resonant Freq. to Characterize Phys. Prop. of Human Long Bone*"; *J. Biomechanics*, 1974, vol. 7, pp. 559-561.

Review Scientific Instruments vol. 50, No. 12, Dec. 1979, pp. 1650, 1651-Cosmelli et al.

*Primary Examiner*—Kyle L. Howell

*Assistant Examiner*—Angela D. Sykes

*Attorney, Agent, or Firm*—Ladas & Parry

[57] ABSTRACT

An apparatus for detecting resonant frequency of bones has an electro-mechanical transducer arranged for application to the external skin surface covering a bone, the transducer being in a feed-back circuit with an amplifier and phase shifter having a unity gain and a loop phase of zero. The feed-back circuit is connected to a display comprising an A-D converter and a digital display. The apparatus displays the lowest order transverse mode set up in a bone.

In a further embodiment the transducer is arranged to pierce the skin and to be in direct contact with a bone. The transducer has a coupling rod and a detector which may be both positioned at the same station on a bone or at spaced stations along a bone.

11 Claims, 1 Drawing Sheet

1
2
7
A/D
152 Hz
8
9
5
3
4
6

APPARATUS FOR DETECTING THE RESONANT FREQUENCY OF A BONE

BACKGROUND OF THE INVENTION

This invention relates to an apparatus for detecting the resonant frequency of a bone and, in particular, although not exclusively, to the resonant frequency of human long bones such as the tibia, femur, radius and ulna.

A need exists to determine the fracture repair of bones and the current medical practice of using X-ray methods requires expert interpretation and normally takes eight weeks to assess a fracture.

It is known that bones have a mechanical resonant frequency and that by striking a bone to set up a frequency therein the resonant frequency may be determined and all bones have such resonant frequencies.

Two main factories determine the resonant frequency of a bone and these are the bones stiffness and mass. The stiffness of a bone when it is repairing after a fracture is less than that of the rest of the bone so that the stiffness of a repairing bone and hence the resonant frequency of that bone are reduced in comparison with the persons non-fractured bone. However, as the bone heals, the stiffness approaches that of an unfractured bone and so the resonant frequency also reverts to its normal value. It is known that a callous eventually forms at the fracture site which provides the bone with a greater mass than the unfractured bone and so the final resonant frequency is slightly lower than that of the original unfractured bone.

SUMMARY OF THE INVENTION

The present invention seeks to provide an apparatus for detecting the resonant frequency of bones which apparatus may be hand-held if desired.

According to one aspect of this invention there is provided an apparatus for detecting the resonant frequency of a bone including an electro-mechanical transducer arranged to resonate the bone and for application to the external skin surface covering the bone, said transducer being in a feed-back circuit with an amplifier means having unity gain and a predetermined loop phase of zero, and a display means connected to receive output signals from the amplifier means for displaying the bone resonant frequency.

Preferably the resonant frequency of the bone displayed is selected by the response of the amplifier means to be the lowest order transverse mode.

Advantageously, a pressure micro-switch is positioned in a path between the electro-mechanical transducer and a bone to be measured, said micro-switch being arranged to close the path at a predetermined pressure, which in the currently preferred embodiment is a pressure of approximately 25g/mm$^2$.

The transducer includes a mechanical coupling rod and a detecting means and in one embodiment the coupling rod and detecting means are the same element positioned at the same station on a bone and in another embodiment they are separate elements positioned at spaced stations on a bone.

Conveniently, the display means includes an analogue/digital converter and a digital display.

According to another aspect of this invention there is provided an apparatus for detecting the resonant frequency of a bone including an electro-mechanical transducer arranged to resonate the bone and for direct application to the bone, said transducer being in a feed-back circuit with an amplifier means having unity gain and a predetermined loop phase of zero, and a display means connected to receive output signals from the amplifier means for displaying the bone resonant frequency.

BRIEF DESCRIPTION OF THE DRAWINGS

The invention will now be described, by way of example, with reference to the accompanying drawings in which.

DESCRIPTION OF THE PREFERRED EMBODIMENTS

Figure 1:
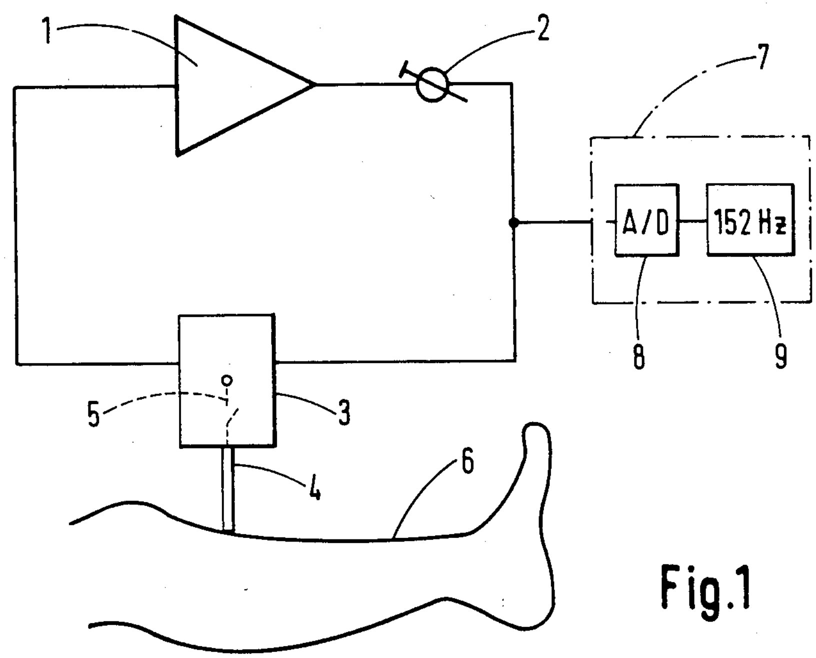
FIG. 1 shows a schematic circuit diagram of the apparatus in accordance with the invention in contact with a human tibia.
Figure 2:
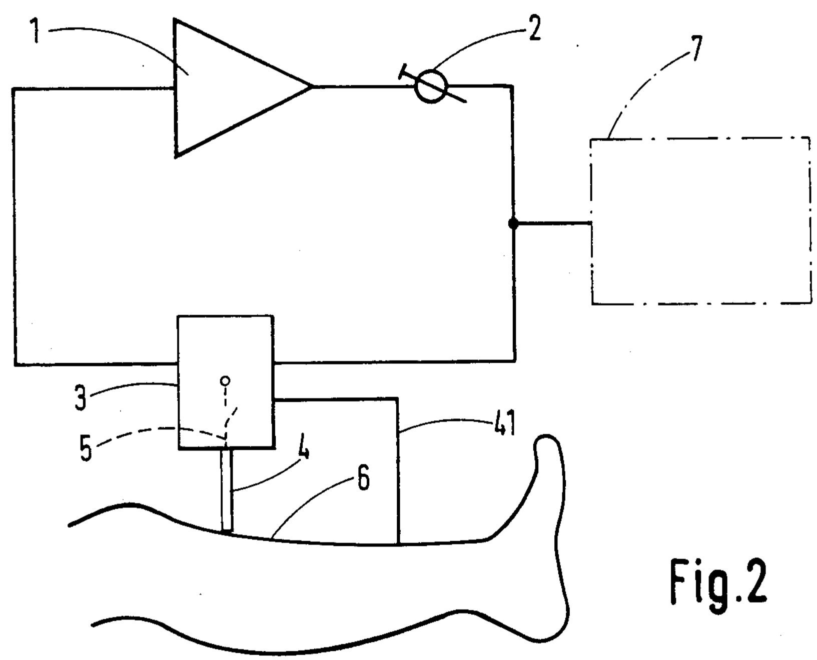
FIG. 2 shows a further embodiment of the invention.

In FIGS. 1 and 2 there is provided an amplifier 1 having a nonlinear gain to avoid saturation and having a frequency response covering the normal range for the bone, for example 100 Hz to 250 Hz and serially connected in a feedback path for the amplifier is a phase shifter 2 and an electro-mechanical transducer 3. The electro-mechanical transducer 3 is arranged to excite a coupling rod 4 through the intermediary of a micro-switch 5 which is arranged to close when a pressure of approximately 25 g/mm$^2$ is applied to the coupling rod 4. In the Figures the coupling rod 4 is shown in contact with the outer surface of the skin of a fractured tibia 6. A display device 7 incorporating an A/D converter 8 connected to a digital display 9 is connected in the feedback path between the phase shifter 2 and electro-mechanical transducer 3.

The present invention is based upon the realisation that the lowest order mechanical resonance in a bone is a transverse mode and no matter where the fracture occurs in the bone the resonance of the bone will be affected. Higher order of frequency modes may have nodes at the fracture site and so may not be detectable. Furthermore, the lowest order mode has been found to appear at an isolated peak in the spectrum or resonances whereas at higher frequency other types of modes, namely longitudinal, make the spectrum of frequencies difficult to identify due to over-lapping resonances.

In operation of the preferred embodiment shown in FIG. 1, the coupling rod 4 is applied to the bone via the external surface of the skin and a pressure of 25 g/mm$^2$ has been found sufficient and to not induce undue pain. The amplifier is chosen to have a gain which will produce a loop gain of unity at the lowest frequency to be measured and the level is fixed to provide sufficient amplitude for a clear signal to be produced. The phase shifter 2 is precalibrated to provide a loop phase of zero.

The electro-mechanical transducer 5 is operated to make the bone 6 resonate and as the bone resonates the phase characteristic of the transducer changes rapidly with frequency. By arranging the phase characteristic of the circuit to have a loop phase of zero so the circuit oscillates at the resonant frequency of the bone, and the frequency of resonance is displayed after A/D converting on the display 9.

The lowest order resonant frequency of the bone is displayed on the display 9 because it is a function of the amplifier 1 to select the lowest order resonant mode.

The apparatus described may, with advantage, be powered by a battery and the whole apparatus formed into a hand-held unit.

In the embodiment of FIG. 2 the transducer 3 has a separate detecting element in contact with the external skin surface of the bone, over line 41 at a different spaced station from the coupling rod 4. such an embodiment may be preferred where the fracture occurs near a joint such as an ankle.

Instead of the rod 4 being in skin contact over a bone, where a person has a thick muscle it is advantageous for the rod 4 to pierce the skin to be brought into actual physical contact with the bone.

Thus, by the present invention the lowest order resonant transverse mode of a fracture bone may be detected and compared with an unfractured bone so that the rate and extent of healing of the fracture may be determined.

It has also been found that by using the apparatus of the present invention general bone disorders, such as calcification and decalcification of bones and tumors may be determined and furthermore that the change in tissue surrounding a bone caused by rheumatism or arthritis may be detected by this invention. The invention is also capable of detecting a loose prosthesis.

In an experimental embodiment:

1. The amplifier 1 was a Radio Spares operational amplifier Type No. 741.
2. The phase shifter 2 was based upon a Radio Spares operational amplifier Type No. 741.
3. The electro-mechanical transducer 3 was a Ling Dynamics Limited Type No. 110.
4. The device 7 contained a Radio Spares CMOS 4 decade counter driver Type No. IC7217, an Intersil Inc. CMOS oscillator controller Type No. ICM7207 and a Radio Spares digital display.

I claim:

1. Apparatus for detecting the resonant frequency of a bone including an electromechanical transducer, said transducer comprising a single probe for application to the external skin surface covering the bone and fixed frequency means for continuously resonating the bone via the probe said transducer being in a feed-back loop circuit with an audio amplifier means and a phase shifter, said audio amplifier means and said phase shifter providing unity gain and a predetermined phase of zero for the loop circuit when said transducer probe is resonating said bone, and a display means connected to receive output signals from the loop circuit for displaying the bone resonant frequency.

2. Apparatus as claimed in claim 1 wherein the resonant frequency of the bone displayed is selected by adjusting the phase shifter to be the lowest order transverse mode.

3. Apparatus as claimed in claim 1 wherein a pressure micro-switch is positioned in a path between the continuously resonating means and the probe, said micro-switch being arranged to close the path at a predetermined pressure.

4. Apparatus as claimed in claim 3 wherein said pressure is approximately 25 g/mm$^2$.

5. Apparatus as claimed in claim 1 wherein the transducer further comprises a mechanical coupling rod and detecting means and wherein the probe and detecting means are the same element positioned at the same point on a bone.

6. Apparatus as claimed in claim 1 wherein the display means includes an analogue/digital converter and a digital display.

7. Apparatus for detecting the resonant frequency of a bone including an electro-mechanical transducer, said transducer comprising a needle-like probe for direct application to the bone through the skin covering the bone and fixed frequency means for continuously resonating the bone via the probe, said transducer being in a feed-back loop circuit with an audio amplifier means and a phase shifter, said audio amplifier means and said phase shifter being arranged to provide unity gain and a predetermined phase of zero for the loop circuit when said transducer probe is resonating said bone, and a display means connected to receive output signals from the loop circuit for displaying the bone resonant frequency, the resonant frequency of the bone displayed being selected by the response of the phase shifter to be the lowest order transverse mode.

8. Apparatus for detecting the resonant frequency of a bone including an electromechanical transducer, said transducer comprising a single probe for application to the external skin surface covering the bone, fixed frequency means for continuously resonating the bone via the probe, and detecting means which is spatially separated from said probe, said transducer being in a feed-back loop circuit with an audio amplifier means and a phase shifter, said audio amplifier means and said phase shifter providing unity gain and a predetermined phase of zero for the loop circuit when said transducer probe is resonating said bone, and a display means connected to receive output signals from the loop circuit for displaying the bone resonant frequency, whereby the probe and said detecting means are arranged to be spatially separated from one another along the length of the bone.

9. Apparatus for detecting the resonant frequency of a bone including an electromechanical transducer, said transducer comprising a needle-like probe for direct application to the bone through the skin covering the bone, fixed frequency means for continuously resonating the bone via the probe, and detector means which is spatially separated from the said probe, said transducer being in a feed-back loop circuit with an audio amplifier means and a phase shifter, said audio amplifier means and said phase shifter being arranged to provide unity gain and a predetermined phase of zero for the loop circuit when said transducer probe is resonating said bone, and a display means connected to receive output signals from the loop circuit for displaying the bone resonant frequency.

10. A method of detecting the resonant frequency of a bone by an apparatus having a feed-back loop circuit comprising an electromechanical transducer including a single probe means arranged to continuously resonant the bone at a fixed frequency, and audio amplifier having unity gain and a phase shifter adjusted to provide the loop circuit with a phase shift of zero when the probe means is resonating said bone, and a display means connected to receive output signals from the loop circuit, said method including the steps of (a) applying the probe means to one if (i) the external skin surface covering the bone and (ii) directly to the bone through the skin covering thereof, and (b) resonating said bone with said probe means, the resonant frequency of said bone being displayed on said display means.

11. A method as claimed in claim 14 wherein a detector means is provided which is spatially separated from said probe and the probe and detector means are spatially separated from one another along the length of a bone, and the detector means detects the lowest order transverse mode of the bone when said bone is being resonated.

* * * * *